US010810758B2

(12) United States Patent
Mandwal et al.

(10) Patent No.: US 10,810,758 B2
(45) Date of Patent: Oct. 20, 2020

(54) METHOD AND SYSTEM USING AUGMENTATED REALITY FOR POSITIONING OF ECG ELECTRODES (71) Applicant: General Electric Company, Schenectady, NY (US)

(72) Inventors: Rajeev Mandwal, Bangalore (IN); Brian J. Young, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 106 days.

(21) Appl. No.: 16/019,778

(22) Filed: Jun. 27, 2018

(65) Prior Publication Data
US 2020/0005481 A1  Jan. 2, 2020

(51) Int. Cl.
*G06T 7/73* (2017.01)
*G02B 27/01* (2006.01)
*A61B 5/00* (2006.01)
*G06T 7/00* (2017.01)
*A61B 5/044* (2006.01)

(52) U.S. Cl.
CPC .............. *G06T 7/73* (2017.01); *A61B 5/044* (2013.01); *A61B 5/684* (2013.01); *G02B 27/0172* (2013.01); *G06T 7/0012* (2013.01); *G06T 2207/10024* (2013.01); *G06T 2207/30196* (2013.01); *G06T 2207/30204* (2013.01)

(58) Field of Classification Search
CPC . G02B 2027/0178; G06T 7/0012; G06T 7/14; G06T 7/16; G06T 19/006
See application file for complete search history.

(56) References Cited

U.S. PATENT DOCUMENTS

| | | | |
|---|---|---|---|
| 9,883,835 B2 | 2/2018 | Xue | |
| 2014/0194760 A1 | 7/2014 | Albert | |
| 2017/0065349 A1* | 3/2017 | Ourselin | A61B 34/10 |
| 2017/0071492 A1 | 3/2017 | Van Dam et al. | |
| 2017/0087364 A1* | 3/2017 | Cartledge | A61N 1/36014 |
| 2017/0112439 A1* | 4/2017 | Dubin | A61B 5/7285 |
| 2017/0301102 A1* | 10/2017 | Urman | A61B 5/0531 |
| 2018/0046245 A1* | 2/2018 | Schwarz | G02B 27/0093 |
| 2018/0322702 A1* | 11/2018 | Djajadiningrat | A61B 5/0404 |
| 2019/0212827 A1* | 7/2019 | Kin | G02B 27/0179 |

* cited by examiner

*Primary Examiner* — Wen W Huang
(74) *Attorney, Agent, or Firm* — Andrus Intellectual Property Law, LLP (57) ABSTRACT A method of directing positioning of ECG electrodes on a patient includes receiving at a processor an image of a patient from a camera of an augmented reality device. The processor analyzes the image for anatomical landmarks on the patient and generates an overlay image. The overlay image is shown over the real time image of the patient on the augmented reality device. The overlay image includes visual indicators of the desired electrode placement. The method further includes determining whether the actual location of each of the electrodes is correct and provides information on the augmented reality device as to whether the electrodes and lead placement is correct. An image of the electrode placement is stored with the ECG measurements, which can be used to verify correct electrode placement and to confirm consistent electrode placement over serial measurements. The augmented reality device allows for gesture control by the clinician.

15 Claims, 10 Drawing Sheets

METHOD AND SYSTEM USING AUGMENTATED REALITY FOR POSITIONING OF ECG ELECTRODES

BACKGROUND

In electrocardiography, correct lead placement is very important and can greatly affect the waveforms obtained by an electrocardiograph (ECG) monitor. Accordingly, clinicians administering ECGs are often well trained on correct electrode placement. There are a multitude of different electrode placement configurations which may be employed in various circumstances for obtaining ECGs, adding to the amount of training and expertise required to properly place electrodes for ECG monitoring. Moreover, comparison of ECG waveforms to ECG waveforms from prior ECG recordings is standard clinical practice for accurate interpretation of ECG recordings. Consequently, consistent lead placement of electrodes for sequential ECG recordings is just as critical as correct lead placement for interpretation of serial changes between sequential ECG recordings.

Moreover, as regular ECG monitoring becomes an increasingly important part of healthcare, tools for providing and detecting proper electrode placement are becoming increasingly important and prevalent. Frequently, clinicians that are inexperienced in administering ECG tests are being called on to administer ECGs, including placing electrodes on patients.

As ECG electrode placement is such a technical and detailed practice, mistakes are commonly made in ECG electrode placement, leading to inaccuracies in ECG monitoring and waveform assessment. A multitude of tools have been developed attempting to determine whether improper electrode placement is causing inaccuracies in recorded ECG waveforms. Many of these tools assess the waveforms themselves in an attempt to assess and identify inaccurate and/or inconsistent lead placement. For example, multiple tools have been developed attempting to detect when electrodes are switched. However, these tools are generally ineffective at identifying problems with electrode placement and discerning the difference between abnormalities in waveforms caused by cardiac issues versus abnormalities resulting from incorrect electrode placement.

Moreover, hospital acquired infections (HAIs) are always a significant concern in monitoring environments. An HAI is an infection that develops as a result of medical care. Due to cross contamination of reusable devices, such as ECG leads and electrodes, outer surfaces of input devices, such as keyboards and touch screens can get contaminated with harmful bacteria and viruses. This cross contamination occurs mainly when clinicians touch the patient's skin and then the input device of the ECG monitor. To prevent cross contamination, cleaning and disinfecting procedures must be followed for each test to achieve the required efficacy. The cleaning and disinfecting procedures are time consuming and do not always provide a satisfactory result and any tools such as proposed in this disclosure, which decreases the amount of patient contact required to successfully perform a test procedure, will help reduce the risk of HAI.

SUMMARY

The present invention alleviates problems recognized by the inventor regarding incorrect and/or inconsistent ECG electrode placement and prior art systems and methods attempting to detect and correct ECG electrode placement. This summary is provided to introduce a selection of concepts that are further described below in the Detailed Description. This summary is not intended to identify key or essential features of the claimed subject matter, nor is it intended to be used as an aid in limiting the scope of the claimed subject matter.

In one embodiment, a method of directing positioning of ECG electrodes on a patient includes providing an augmented reality device that includes both a camera and at least one display. The method receives a real time image of a patient before the electrodes are positioned on the patient. The real time image can be a still image, or in a preferred embodiment, a video image of the patient, which can be used both for identification of anatomical landmarks to guide correct electrode placement, as well as image registration to spatially align images from sequential test procedures.

The method analyzes the real time image from the augmented reality device to identify anatomical landmarks on the patient. Based on the anatomical landmarks, an overlay image is generated that includes visual representations of desired locations for the electrodes. In addition, the anatomical landmarks can be used for registration of images from serial tests so that consistency of electrode placement can be measured between sequential tests from the same patient. The overlay image is displayed over the real time image of the patient on the display of the augmented reality device to aid in positioning of the electrode on the patient.

Once the electrodes have been positioned on the patient, the method receives an image of the patient with the actual location of the positioned electrodes. The method then compares the actual location of the electrodes and the desired location of the electrodes to confirm the correct positioning of the electrodes before the ECG is taken.

After the positioning of the electrodes is confirmed to the clinician, the clinician can connect the lead wires to the electrodes. In one embodiment, the electrodes and lead wires each include indicators that help match the lead wires to the electrodes. After the lead wires are connected, an image of the connections is received and analyzed to determine whether the proper connections have been made in terms of both accurate and consistent electrode placement. Clinical situations may be encountered whereby proper location of an electrode is not possible because of an unusual or exigent medical need. In such cases, it is desirable and important to use consistent electrode placement when the standard electrode position cannot be used. If the connections are not correct, the system and method generates an overlay image that includes instructions for the clinician to modify the connections. If the connections are correct, the overlay image will include a visual indicator confirming the connections to the clinician.

One embodiment of a system for directing positioning of electrodes on a patient includes an augmented reality device having at least a camera and a display, one or more electrodes, and a positioning analysis module. The positioning analysis module is executable by a processor to receive an image taken with the camera of a patient's chest before the electrodes have been placed thereon. The positioning analysis module obtains an overlay image which includes a visual representation of desired location for the electrodes. The overlay image, in some embodiments, can also include anatomical landmarks to further aid in training and electrode placement. The overlay image is displayed with the real time image of the patient on the display of the augmented reality device.

The system is further operable to determine whether the electrodes and lead wires have been properly positioned on the patient and generate either further instructions or confirmation to the clinician. In some embodiments, the system allows the clinician to perform hand gestures within the field of view of the camera to initiate various function of the ECG monitoring device. The use of hand gestures eliminates the requirement that the clinician touch an input device, such as a keyboard or touch screen, which reduces the possibility of cross contamination. One of more visual representation of the possible hand gestures are included as part of the overlay image to provide information to the clinician.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION

Figure 1A:
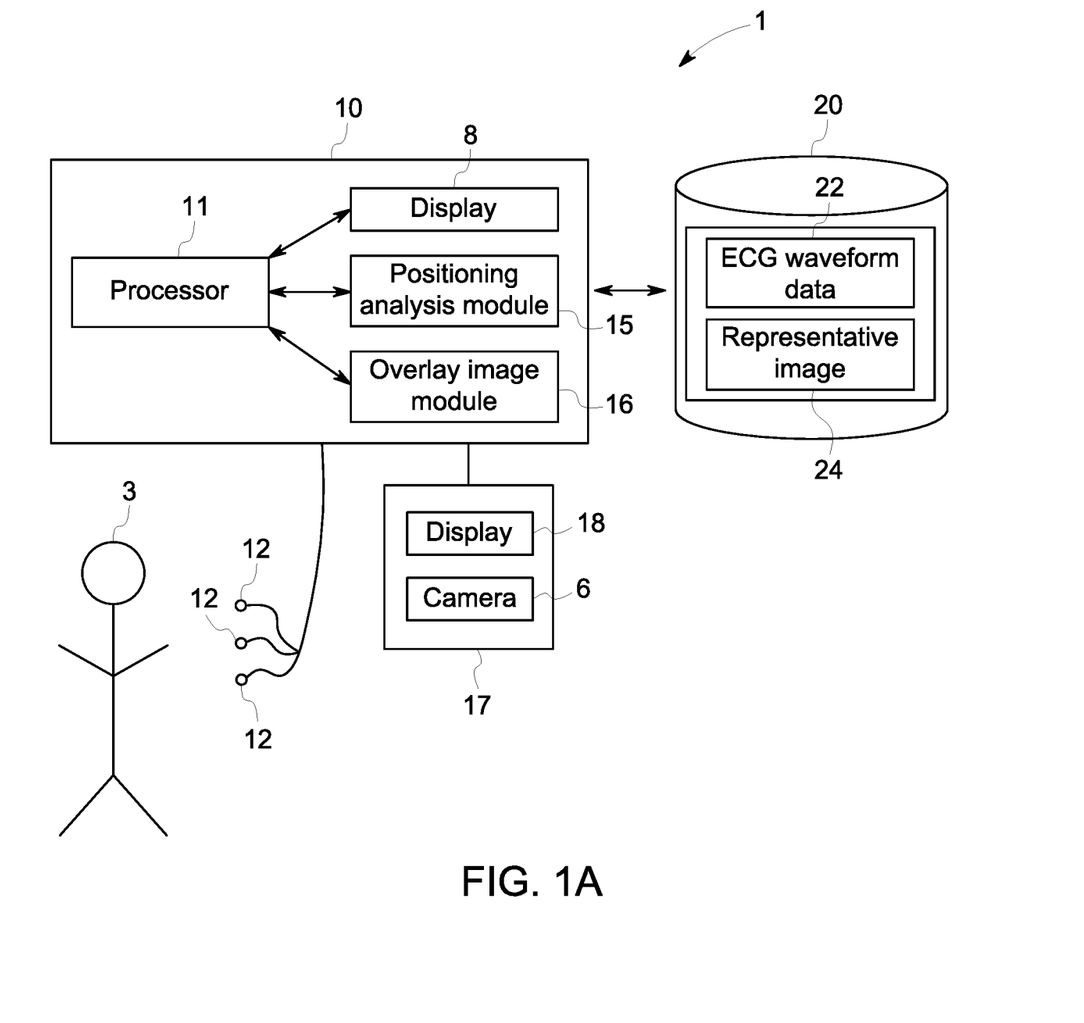
FIG. 1A depicts one embodiment of a system for directing positioning of ECG electrodes on a patient.
Figure 1B:
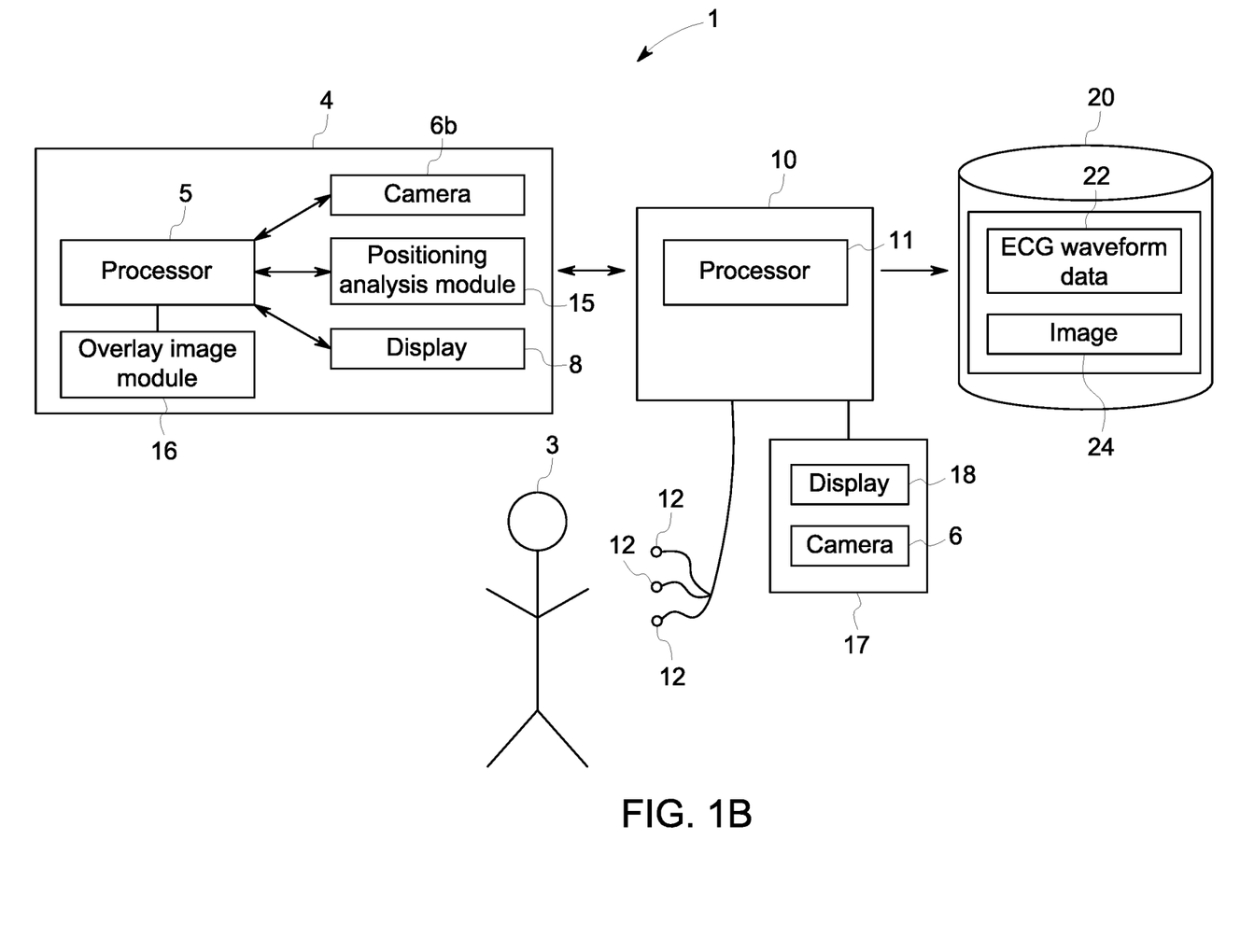
FIG. 1B depicts another embodiment of a system for directing position of ECG electrodes on a patient.
Figure 2:
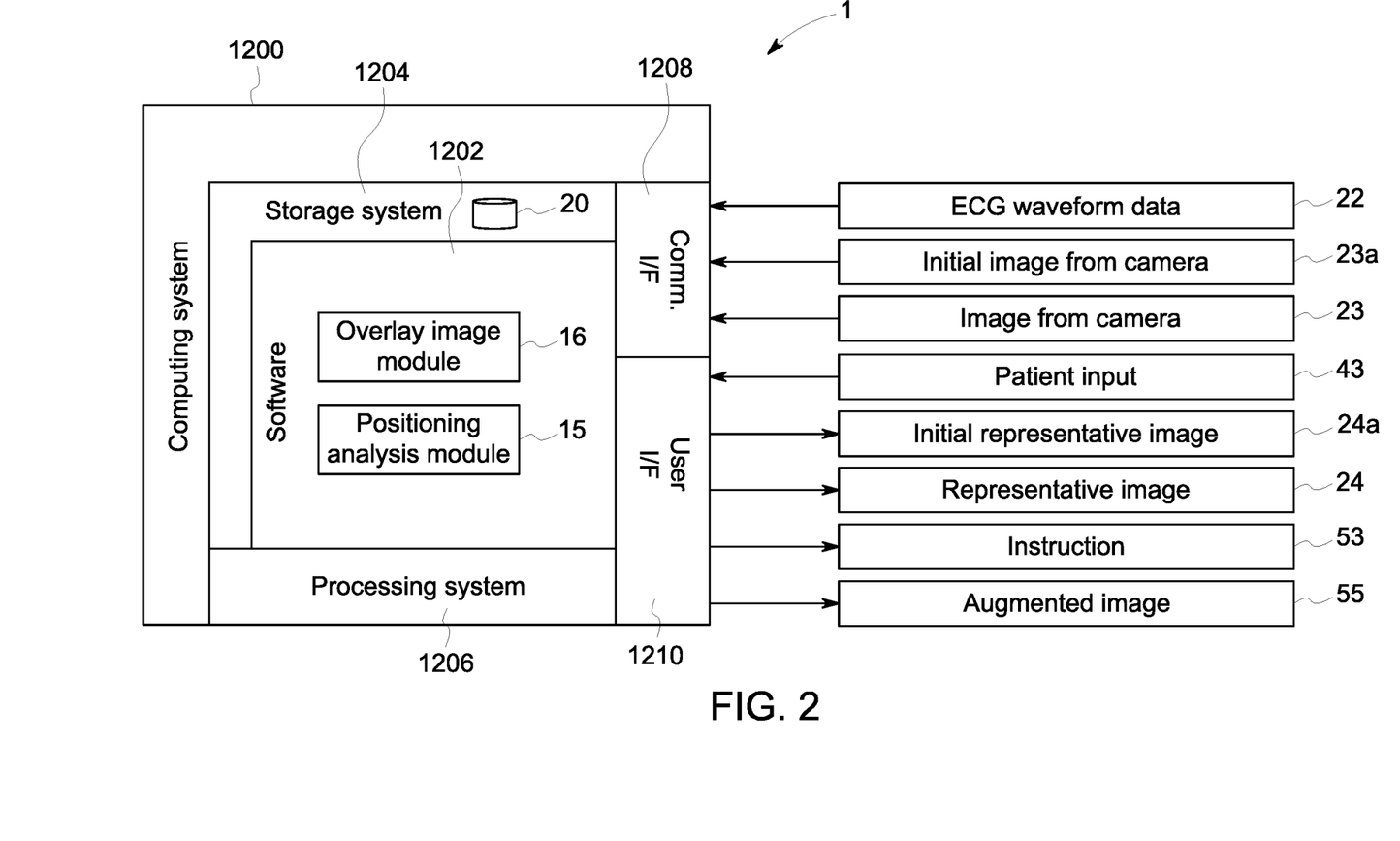
FIG. 2 depicts another embodiment of a system for directing position of ECG electrodes on a patient.
Figure 3:
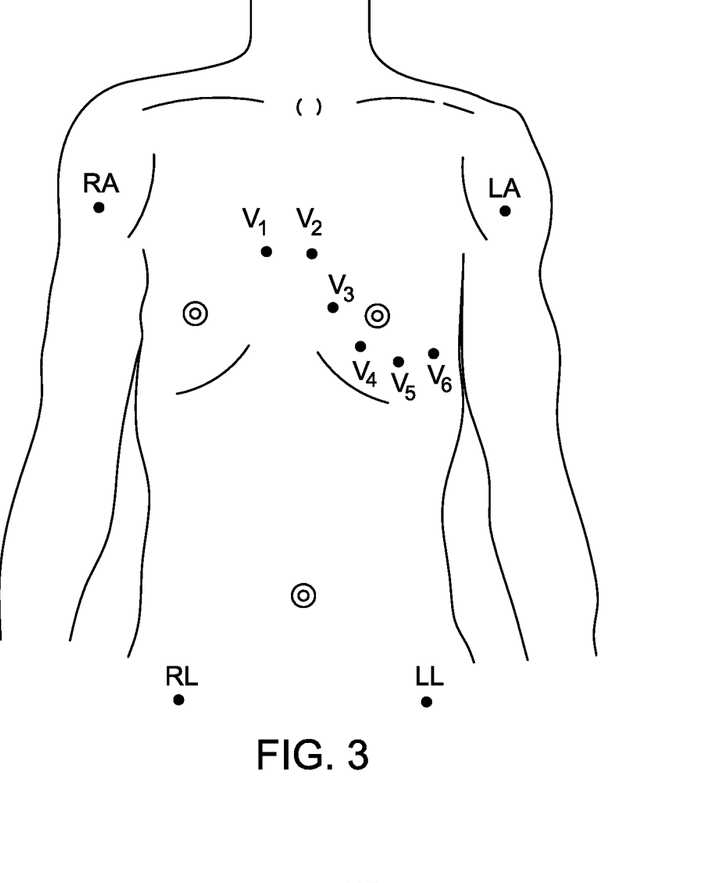
FIG. 3 depicts the exemplary representative image of a patient's chest with desired electrode locations marked thereon.

FIGS. 1A, 1B and 2 depict various embodiments of a system for directing positioning of ECG electrodes on a patient in real time. In the embodiment of FIG. 1A, the system 1 for directing placement of ECG electrodes includes an ECG monitor 10 connected to electrodes 12. For ease of depiction, three electrodes 12 are included in the figure; however, one of skill in the art will understand that any of various numbers of electrodes 12 may be utilized to obtain an ECG recording. In a common example, ten electrodes 12 are placed on the patient 3 in a standard 12-lead ECG arrangement. By way of example, FIG. 3 depicts an exemplary standard 12-lead ECG arrangement, which has six precordial electrodes (V1-V6) and four limb electrodes (RA, LA, RL, LL) in the preferred location for each. Other ECG electrode and lead configurations are known in the art, including configurations using three, four, or five ECG electrodes.

In the embodiment of FIG. 1A, the ECG monitor 10 includes a processor 11 connected to display 8. In the embodiment shown, an augmented reality device 17, including at least one display 18 and a camera 6, is corrected to the ECG monitor 10. The processor 11 is configured to enable access and execution of the positioning analysis module 15 and an overlay image module 16. The system 1 also includes database 20 housing ECG waveform data 22 and an image 24 of the chest of the patient 3 with the electrodes 12 positioned thereon. For example, image 24 may be stored with the ECG waveform data 22, such that the image 24 depicts the electrode arrangement on the chest of the patient 3 that was used to record the ECG waveform data 22. The image 24 may further be stored with the ECG waveform data 22 such that it is accessible by a clinician viewing the ECG waveform data 22 so that the clinician can view how the electrodes 12 were placed on the patient 3 when the ECG waveform data 22 was recorded. This may provide information to the clinician that may be valuable in correctly interpreting the data.

Anatomical landmarks in the recorded image for each set of ECG waveform data 22 can be used for the registration of images from serial tests. The registration and comparison information can be used to determine the consistency of electrode placement between sequential tests from the same patient. The consistency of lead placement and electrode location for sequential ECG recordings may be as critical as correct lead placement for the interpretation of serial changes between sequential ECG recordings.

As is described in greater detail below, the camera 6 of the augmented reality device 17 is used to capture a real time image of the patient 3 before and after the electrodes 12 are placed on the patient's chest. The positioning analysis module 15 is then executed on the processor 11 to analyze the real time image captured by the camera 6 to determine whether the electrodes 12 are placed correctly. The positioning analysis module 15 further directs the real-time provision of information to a clinician administering an ECG on the patient 3, regarding the location of the electrodes 12. For example, the positioning analysis module 15 may display a superimposed image obtained from the overlay image module 16 showing the desired electrode placement over the image of the patient using the display 18 with instructions regarding adjustment of the location of one or more of the electrodes 12 on the patient's chest.

Figure 4:
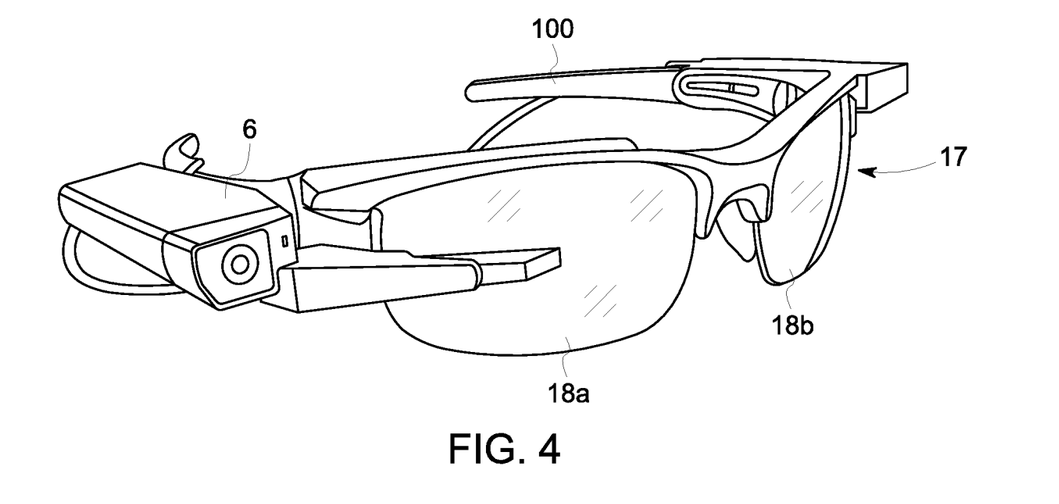
FIG. 4 depicts an exemplary representation of an augmented reality device in accordance with the present disclosure.

In one embodiment of the disclosure, the augmented reality device 17 is shown in FIG. 4 as a pair of augmented reality glasses 100. The glasses 100 include the camera 6 and one or more displays 18a, 18b. The augmented reality glasses 100 can be connected to the ECG monitor 10 either using a hardwired connection or can communicate with the ECG monitor 10 using any type of wireless communication techniques, such as but not limited to Bluetooth communication. Although the augmented reality device 17 is shown in FIG. 4 as being a pair of glasses 100 including the displays 18a and 18b, other types of augmented reality devices 17 could be utilized, such as a personal computing device, including smartphones, as will be described in much greater detail below. The augmented reality glasses 100 are used to obtain a real time image as seen by the clinician through the camera 6 and to display augmented images to the clinician using one or both of the displays 18a and 18b. Further details of the augmented images projected onto the displays 18a, 18b will be described below.

In the embodiment of the system 1 depicted in FIG. 1B, the system 1 further includes a personal computing device 4 having its own processor 5, camera 6b and display 8. The personal computing device 4 may be configured to store, access, and execute the positioning analysis module 15 and access the overlay image module 16. In this embodiment, the personal computing device 4 functions as an augmented reality device. For example, the personal computing device 4 may be a smartphone, tablet, or laptop, and the positioning analysis module 15 and overlay image module 16 may be software stored thereon. In one specific example, the positioning analysis module 15 may be an application stored in memory on the personal computing device 4 and executable by the processor 5 of the personal computing device 4 to perform as described herein, including displaying instructional images and to the clinician on the display 8 regarding electrode positioning. In the embodiment of FIG. 1B, the personal computing device 4 is communicatively connected to the ECG monitor 10, and the ECG monitor 10 is communicatively connected to the database 20. The system 1 of FIG. 1B may be configured to utilize the camera 6 connected or associated with the augmented reality device 17 and/or the camera 6b and display 8 on the personal computing device 4 to capture the one or more images 24 as described herein. In a preferred embodiment, the camera 6 is a 3D camera capable of capturing a three-dimensional image of the patient 3. However, it is also contemplated that the camera 6 may alternatively be a standard camera capturing two-dimensional images, or photographs, or a video camera, or an infrared imager or camera. Likewise, the camera 6b in the personal computing device 4 may be any type of camera, including a 3D camera, a standard 2D camera, a video camera, or an infrared camera or imager. For example, the camera 6b may be a 3D camera device that connects to personal computing devices 4, like smartphones or tablets, which are known and available in the art.

FIG. 2 depicts another embodiment of a system 1 for directing ECG electrode placement. FIG. 2 provides another system diagram of an exemplary embodiment of the system 1 for directing positioning of ECG electrodes including a positioning analysis module 15 and overlay image module 16 executable to provide information and augmented images regarding electrode positioning as described herein. The system 1 includes a computing system 1200 that includes a processing system 1206, storage system 1204, software 1202, communication interface 1208 and a user interface 1210. The processing system 1206 loads and executes software 1202 from the storage system 1204, including the positioning analysis module 15 and the overlay image module 16, which are applications within the software 1202. The positioning analysis module 15 includes computer-readable instructions that, when executed by the computing system 1 (including the processing system 1206), the positioning analysis module 15 directs the processing system 1206 to operate as described in herein in further detail, including to execute the steps of receiving an image 23 of the patient 3 from the camera 6, generating the augmented image obtained from the overlay image module 16 on a display over the obtained image, determining the actual location of each electrode 12 on the patient's chest, determining whether the actual location is correct, providing information to the patient regarding the actual locations of the electrodes, and storing the image(s) 24 of the patient's chest along with the ECG waveform data 41 in database 20.

Although the computing system 1200 as depicted in FIG. 2 includes one software 1202 encapsulating one positioning analysis module 15 and one overlay image module 16, it should be understood that one or more software elements having one or more modules may provide the same operation. Similarly, while description as provided herein refers to a computing system 1 and a processing system 1206, it is to be recognized that implementations of such systems can be performed using one or more processors, which may be communicatively connected, and such implementations are considered to be within the scope of the description.

The processing system 1206 comprises processor 11 and/or processor 5, which may be microprocessors and other circuitry that retrieves and executes software 1202 from storage system 1204. Processing system 1206 can be implemented within a single processing device but can also be distributed across multiple processing devices or sub-systems that cooperate in existing program instructions. Examples of processing system 1206 include general purpose central processing units, application-specific processors, and logic devices, as well as any other type of processing device, combinations of processing devices, or variations thereof.

The storage system 1204, which includes the database 20, can comprise any storage media, or group of storage media, readable by processing system 1206, and capable of storing software 1202. The storage system 1204 can include volatile and non-volatile, removable and non-removable media implemented in any method or technology for storage of information, such as computer-readable instructions, data structures, program modules, or other data. Storage system 1204 can be implemented as a single storage device but may also be implemented across multiple storage devices or sub-systems, which may be accessible to the processor(s) 5, 11. For example, the software 1202 may be stored on a separate storage device than the database 20. Storage system 1204 can further include additional elements, such a controller capable, of communicating with the processing system 1206.

Examples of storage media include random access memory, read only memory, magnetic discs, optical discs, flash memory, virtual memory, and non-virtual memory, magnetic sets, magnetic tape, magnetic disc storage or other magnetic storage devices, or any other medium which can be used to storage the desired information and that may be accessed by an instruction execution system, as well as any combination or variation thereof, or any other type of storage medium. In some implementations, the store media can be a non-transitory storage media. In some implementations, at least a portion of the storage media may be transitory.

The user interface 1210 is configured to receive input 43 from a clinician, and to generate one or more instructions 53 to the clinician. User interface 1210 can include a mouse, a keyboard, a voice input device, a touch input device for receiving a gesture from a user, a motion input device for detecting non-touch gestures and other motions by a user, and other comparable input devices and associated processing elements capable of receiving user input from a user. Output devices such as a video display or graphical display can display instructions 53 and augmented images 55 and an interface further associated with embodiments of the system and method as disclosed herein. Speakers, printers, haptic devices and other types of output devices may also be included in the user interface 1210.

As described in further detail herein, the system 1 receives one or more real time images 23 from the camera 6, and may also receive the patient's ECG waveform data 22. The image may be, for example, an image file, such as in the .jpg, .gif, .tiff, .bmp formats, or similar, or a video file, such as .webm, .gif, .mov, .wmv, .webm, .mp4 formats, or similar. The patient's ECG waveform data 22 may be recorded by patient monitor 10 through electrodes 12, which may be in analog or digital form. In still further embodiments, the patient's ECG waveform data 26 may be a streaming analog input received in real time or near-real time by the system 1.

Figure 5:
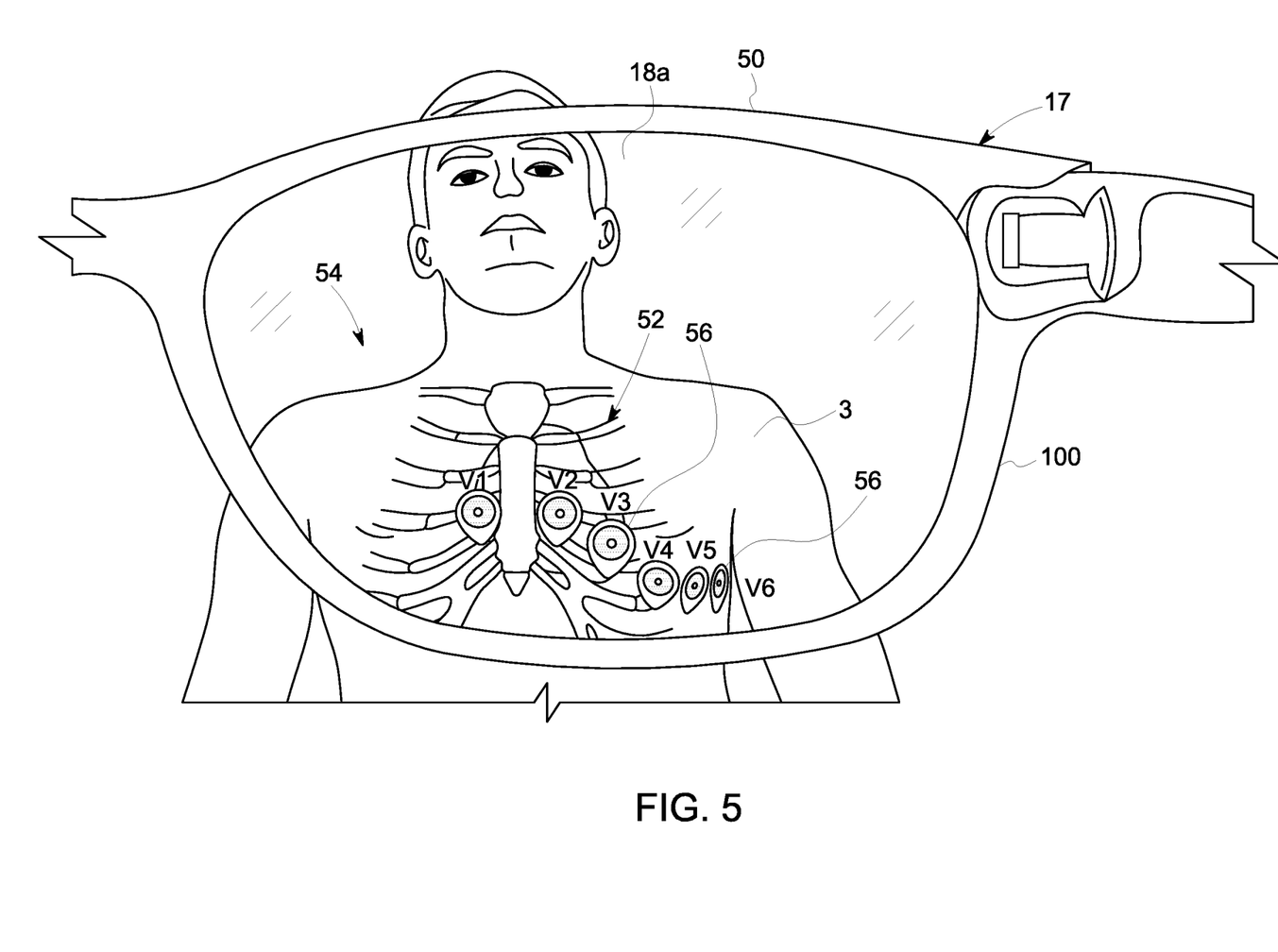
FIG. 5 depicts an augmented image of a patient shown in real time.

FIG. 5 illustrates a real time image 50 viewed by the clinician when utilizing the augmented reality device 17 of the present disclosure. As discussed previously, in the embodiment illustrated, the augmented reality device 17 is a pair of glasses 100 that include lenses that form the pair of displays 18a and 18b. In the embodiment shown in FIG. 5, the clinician can view the patient 3 through the display 18a. The real time image 50 viewed through the display 18 is detected by the camera 6 and relayed to the positioning analysis module 15 of the ECG monitor 10. The processor 11 contained within the ECG monitor 10 coordinates image analysis with the positioning analysis module 15 to identify landmarks on the patient. These landmarks may include creating an outline image of the patient 3 which identifies anatomical locations such as the shoulder, neck, arms and boundaries of the chest cavity. It is contemplated that the positioning analysis module 15 would create an outline of the patient, which would define the orientation of a patient, size of the chest cavity, location of the chest cavity relative to the arms and shoulders.

The positioning analysis module 15 would then communicate to the overlay image module 16 to retrieve and generate an overlay image 52 that would be presented to the clinician on the display 18a. The overlay image 52 would be layered over the real time image 50 to create the augmented image 54 shown in FIG. 5. In the embodiment shown in FIG. 5, the overlay image 52 includes a graphical image of hidden anatomical structures of the patient, such as ribcage, sternum and clavicle bones. The overlay image 52 further includes visual representations of desired positions 56 for the precordial electrodes used in a standard 12-lead ECG. These standard precordial electrodes include the V1, V2, V3, V4, V5 and V6 chest electrodes. If the clinician shifts his or her field of view, the overlay image 52 would shift and show the desired locations for the four limb electrodes RA, LA, RL and LL or locations for alternative lead sets that may be selected by the clinician such as right sided precordial leads V3r, V4r, or V5r (not shown in Figures). As can be understood in the augmented image 54 shown in FIG. 5, the augmented image 54 provides both the real time image of the patient 3 with the overlay image 52 of the desired electrode positions superimposed over the patient. The desired positions provide location information for the electrodes relative to the anatomically significant structures of the patient, such as the sternum and individual ribs of the ribcage. By presenting this information, the system of the present disclosure is able to not only aid in accurate electrode placement for ECG recording but also train less experienced clinicians in lead placement by providing target locations on the patient as the clinician is actually viewing the patient.

In one embodiment, the desired location markers 56 at the desired locations may each be depicted in a unique, predetermined color that is the same color as the corresponding electrode that the patient 3 will place on their chest. For example, the desired location markers 56 may follow the color coding used by the American Heart Association or by the International Electrotechnical Commission. The initial overlay image 52 with the desired location markers 56 may then be displayed to provide a guide, or example, of proper electrode 12 placement that is specifically tailored to the patient's body.

During the initial placement of the electrodes, the processor simultaneously communicates with the image from the camera 6 and the positioning analysis module 15 such that as the clinician shifts his or her viewing direction, the overlay image 52 is modified and sent to the display 18 of the augmented reality device 17. In this manner, the processor and positioning analysis module 15 are able to display the overlay image and the real time image in real time as the viewing focus of the clinician changes.

Figure 6:
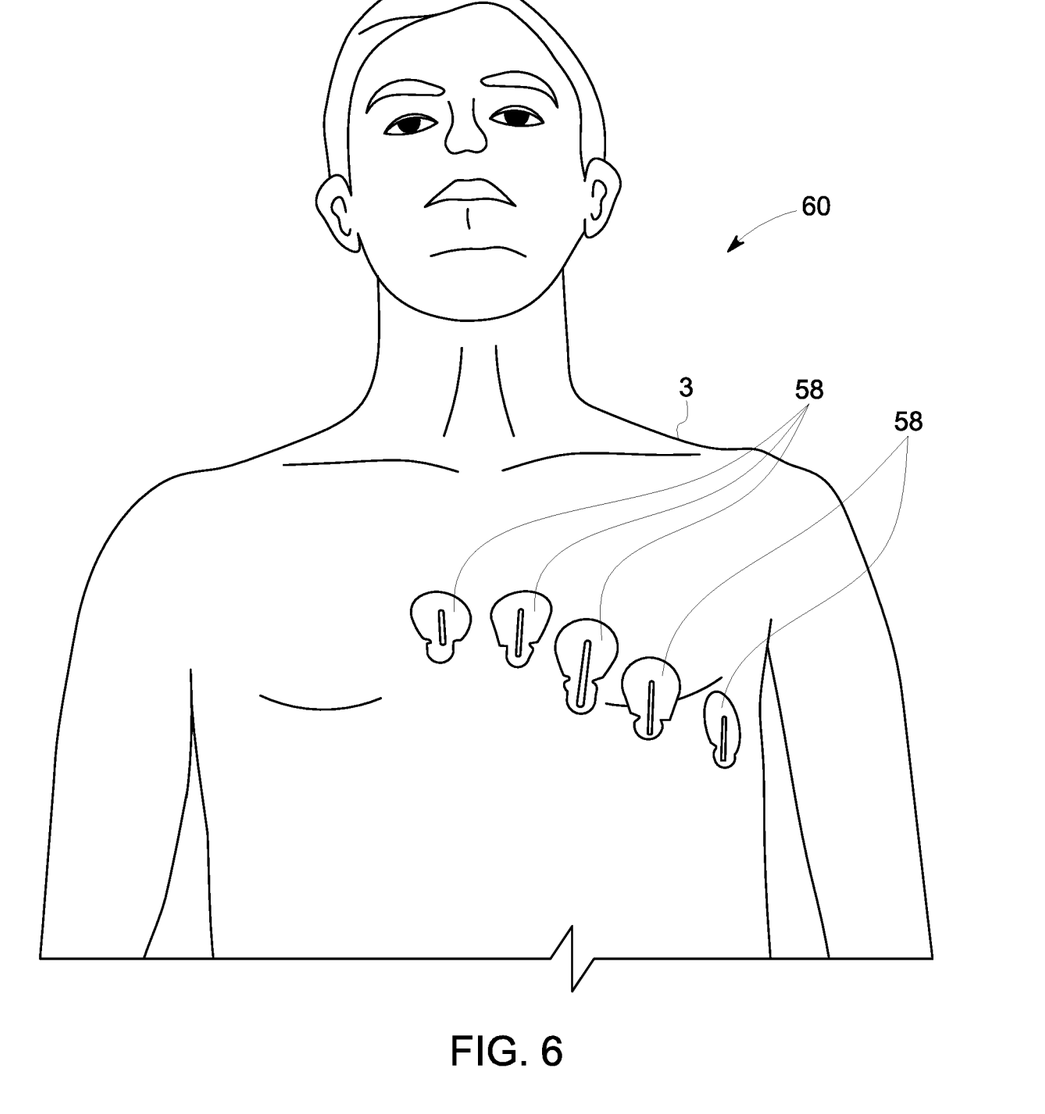
FIG. 6 is a stored image of a patient after electrodes have been applied utilizing the overlay image generated in accordance with the present disclosure.

Referring now to FIG. 6, each of the electrodes 58 are shown positioned in the correct anatomical locations on the patient 3 and a visual image 60 of the electrode placement can be taken by the camera 6 and stored in the database 20. The stored visual image 60 provides visual confirmation of the electrode placement on the patient, which can be useful in analyzing the patient's ECG waveform data 22 at a later time.

It is contemplated that each of the electrodes 58 could include some type of unique marking to help identify the specific electrode. As an example, each of the chest electrodes V1-V6 could include a unique color, reflective image or reflective marking indicating which electrode is which. The reflective markings or coloring would be unique to each different electrode such that the positioning analysis module would be better able to identify which electrode is positioned at each of the locations.

As described above, the visual identifiers may be, for example, color coding, such as according to national or international standards for ECG electrode color coding. In such an embodiment, the physical electrode 12 that the patient places on themselves or that the clinician places on the patient, will contain these visual identifiers, such as color coding, so that the positioning analysis module 15 can identify each electrode. Alternatively or additionally, the visual identifier may be an alphanumerical label, such as "V1," "V2," "V3," etc. Alternatively or additionally, each electrode 12, such as V1-V6, RA, LA, RL, and LL, may be illuminable, which may further assist the positioning analysis module 15 in identifying which electrode 12 is which. For example, each electrode 12 may illuminate in the designated color. Further, the electrodes 12 may be separately illuminable such that the system could illuminate each electrode 12 in a pattern, which could be captured by the system and used to identify and verify the actual location 47 of each respective electrode. For example, the system 1 may be configured such that the camera 6 is configured to capture an image each time an electrode illuminates. In an embodiment where the camera 6 includes a video camera, the system 1 may operate such that the pattern of illumination of each electrode 12, such as V1-V6, RA, LA, RL, and LL, is captured on video.

Figure 7:
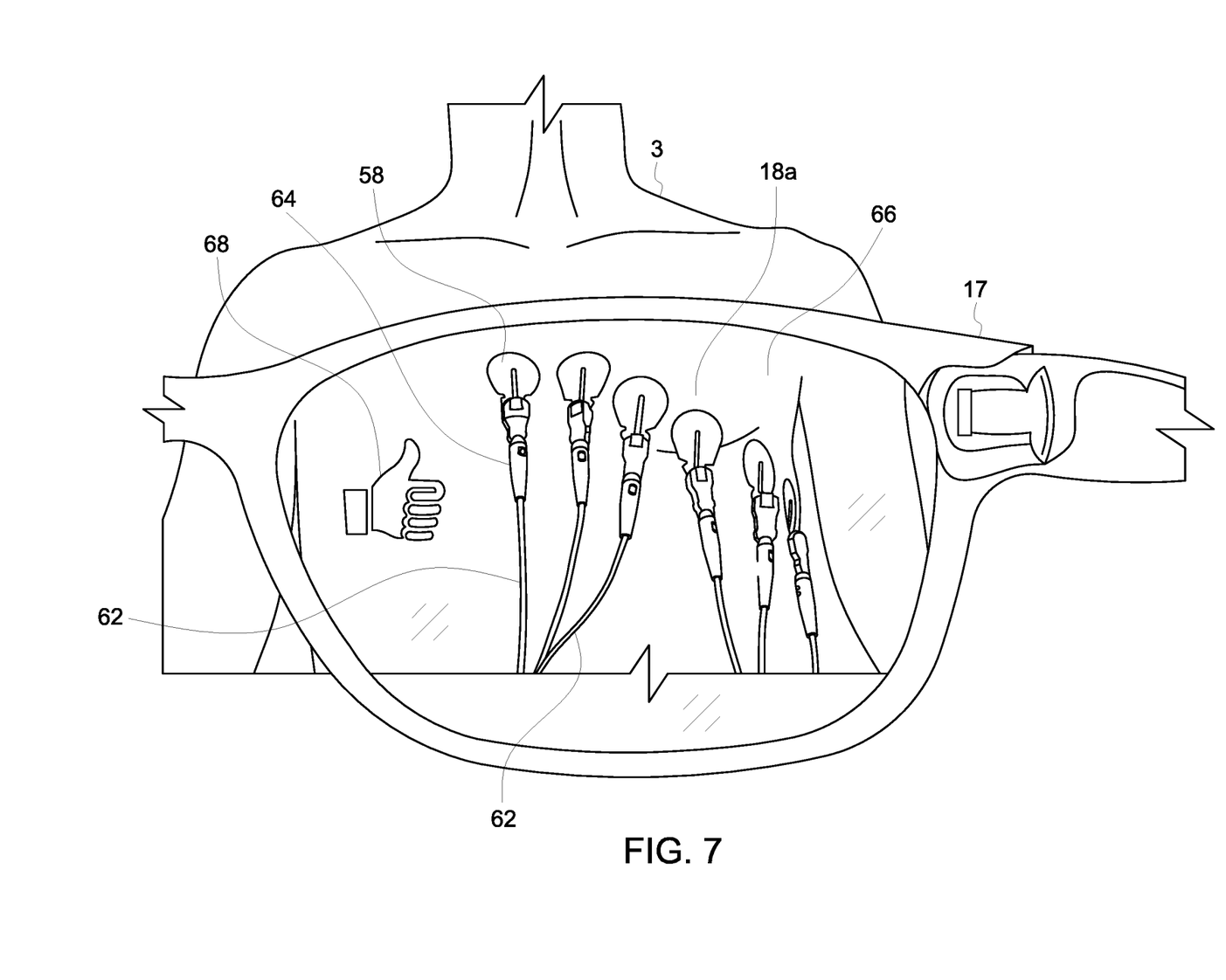
FIG. 7 is an augmented image indicating proper electrode and lead placement.

Once the electrodes have been placed, the clinician begins to connect the individual lead wires 62 to the electrodes 58. In the embodiment shown in FIG. 7, each of the lead wires 62 includes a connector portion 64. The connector portion 64 can also include a visual identifier such as color coding or some type of reflective symbol or identifier. As an illustrative example, the connector portion 64 for electrode V1 will have the same color coding or reflective image as the electrode 58. When the clinician views the chest cavity of the patient through the augmented reality device 17, the patient image 66 is processed by the positioning analysis module of the ECG monitor to verify that the correct lead wires 62 are connected to the corresponding electrodes 58. If the positioning analysis module determines that the lead wires are connected to the correct electrodes, the system can access the overlay image module to retrieve a verification indicator 68 that is overlaid over the real time image. The use of the verification indicator 68 on the display 18a provides immediate feedback to the clinician that the electrodes and lead wires have been connected correctly. In the embodiment shown in FIG. 7, the verification indicator 68 is a universal "thumbs up" icon that may be colored green to indicate that the electrodes and lead wires have been positioned and connected correctly.

Figure 8:
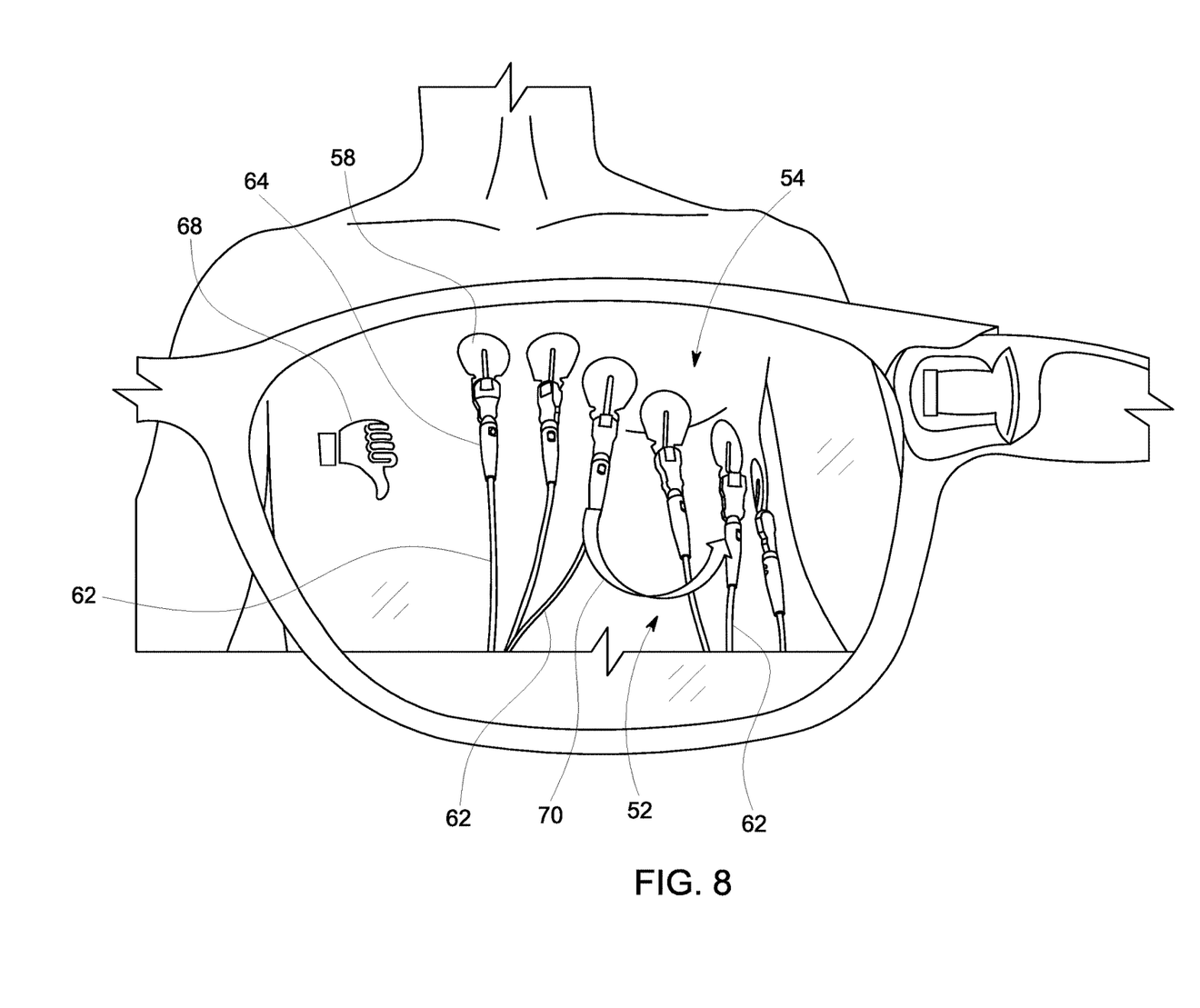
FIG. 8 is an augmented image indicating improper lead connection with the overlay image providing visual instruction to the clinician.

However, if the positioning analysis module determines that the lead wires have not been connected correctly, a different verification indicator will be retrieved from the overlay image module and shown to the clinician indicating that either the electrodes have not been positioned correctly or the lead wires 62 are incorrectly connected. In the example shown in FIG. 8, two of the lead wires 62 are incorrectly connected. The overlay image 52 includes not only the negative verification indicator 68 but also a visual instruction indicator 70. The visual instruction indicator 70 shown in FIG. 8 indicates that the electrode wires for leads V3 and V5 need to be interchanged. Such determination is made by the positioning analysis module 15 based upon a comparison of indicators on each of the electrodes and the connector portions 64 of the lead wires 62. The use of the augmented image 54 allows the clinician to receive specific feedback and instructions in real time while the clinician is viewing the patient. Once again, such real time feedback and instructions while the clinician is viewing the patient allows the clinician to not only confirm electrode and lead placement, but also aids in training less experienced clinicians in ECG electrode placement.

Once the electrode placement and lead connections have been verified, the ECG monitor 10 records an image of both the electrode placement and lead connections which is stored in the database 20 along with the ECG waveform data after the ECG waveform data is collected from the patient. It is contemplated that multiple different images can be stored during the ECG monitoring procedure, including the electrode placement and the lead wire connections. The stored images will aid in ensuring that the ECG data recorded from the patient is taken from correct locations with correct lead wire connections.

As mentioned above, anatomical landmarks in the recorded image for each set of ECG waveform data can be used for the registration of images from serial tests. The recorded images could include just the electrode placement or could also include the lead wire connections. In each case, the registration of the images can be use in a comparison step to determine the consistency of electrode placement between sequential tests from the same patient. The consistency of lead placement and the actual electrode location for sequential ECG recordings may be as critical as correct lead placement for the interpretation of serial changes between sequential ECG recordings.

Figure 9:
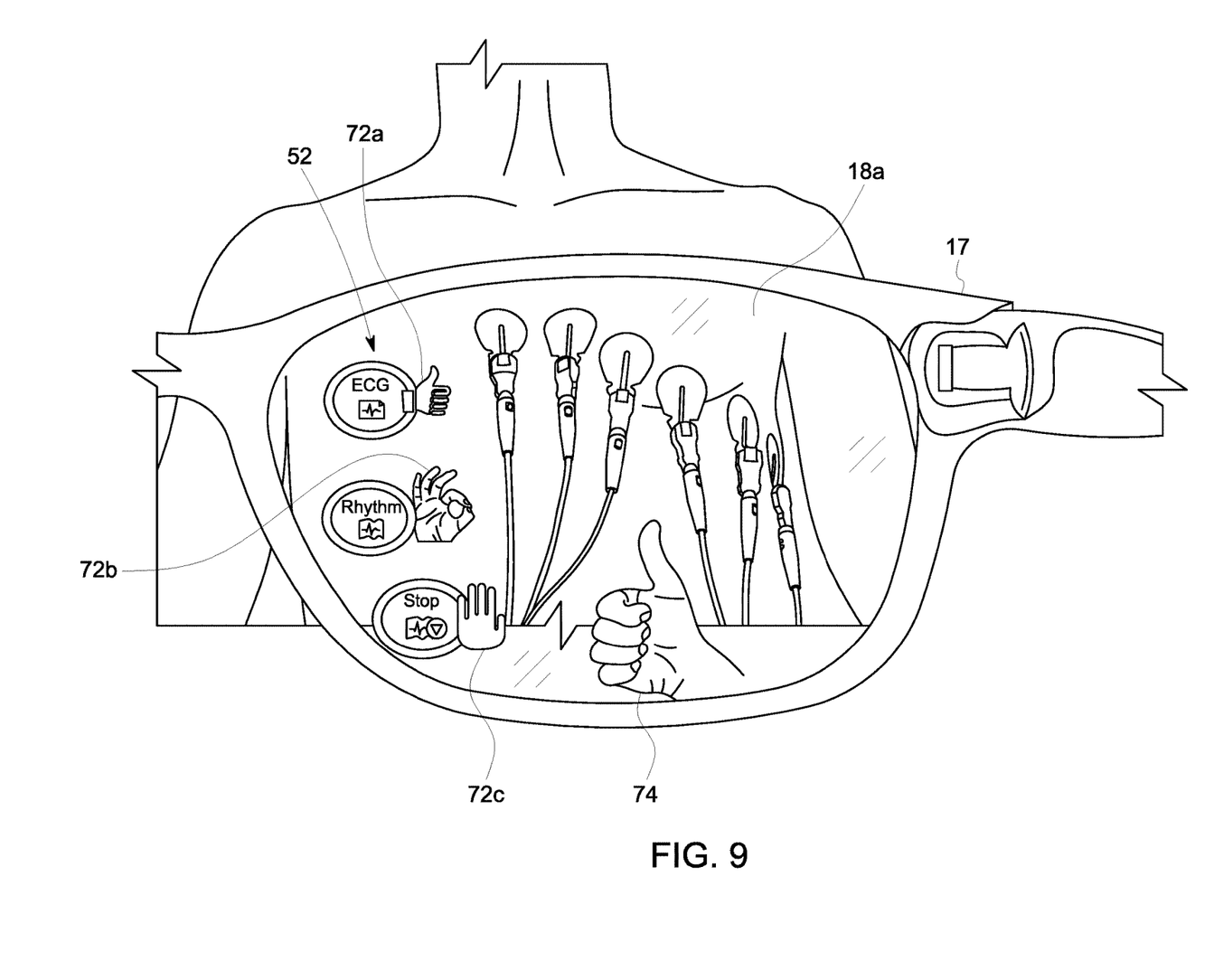
FIG. 9 is an augmented image showing various gesture images and an activation gesture by the clinician.

FIG. 9 depicts another type of operation that can be carried out and performed utilizing the augmented reality device 17 of the present disclosure. In addition to displaying the overlay image 52, the positioning analysis module and processor of the ECG monitor 10 can also provide gesture controls based upon movements of the clinician's hands within the field of view of the camera 6. In the embodiment shown in FIG. 8, the overlay image 52 includes three separate gesture images 72a, 72b and 72c that relate to gestures can be performed by the clinician and carried out by the ECG monitor. The first gesture image 72a is a thumbs up. When the clinician performs a thumbs up gesture, as shown by reference numeral 74, within the field of view of the camera, the positioning analysis module and processor of the ECG monitor will begin the ECG monitoring procedure. The use of the gesture control allows the clinician to begin an ECG recording without having to divert attention from the patient or reaching over to the ECG monitor.

The gesture image 72b is the conventional "okay" hand gesture. When the positioning analysis module and processor identify that the clinician has made the "okay" gesture, they can control the "rhythm" procedure carried out by the ECG monitor. The third gesture image 72c is the stop indicator. The stop gesture requires the clinician to hold their hand out in front of the field of view of the camera. When the ECG monitor senses the hand out gesture, the ECG recording will stop. Use of the gesture control through the overlay image 52 shown on the display 18a and while using the camera 6 allows the clinician to carry out several functions without having to remember the gestures and without having to divert attention away from the patient. In addition, the use of gesture control reduces or completely avoids any contact required between the clinician and an input device, such as a keyboard or touch screen, as was previously needed when taking the ECG and thus reduces any cross-contamination risks.

Although a pair of glasses is shown in FIGS. 4-8 as being one embodiment of the augmented reality device 17, it is contemplated that the augmented reality device could be other types of devices that include both a display and a camera. As an illustrative example, the augmented reality device could be a smartphone, tablet or laptop computer. When using a smartphone as the augmented reality device 17, the clinician would hold the camera of the smartphone in a position such that the clinician could view the patient through the display on the smartphone. The display on the smartphone would then include the overlay image 52 on top of the real time image, thus creating the augmented image. Although a smartphone would function as the augmented reality device, it is contemplated that the glasses shown in FIG. 4 would provide the greatest mobility for the clinician and present the overlay image to the clinician in the most effective manner.

Figure 10:
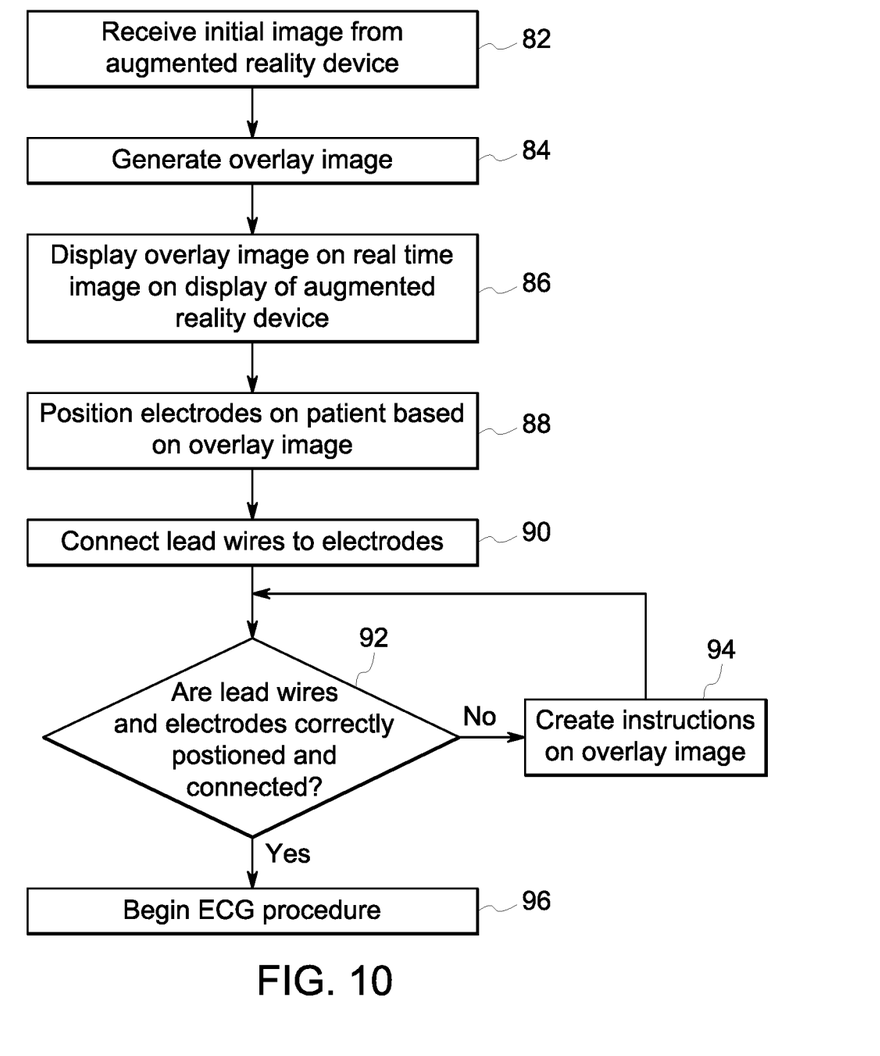
FIG. 10 depicts one embodiment of a method of directing electrode positioning in accordance with the present disclosure.

FIG. 10 depicts one embodiment of a method 80 for directing the positioning of ECG electrodes on a patient in accordance with the present disclosure. The method 80 of FIG. 10 receives an initial real time image from the camera of the augmented reality device 17 as indicated in step 82. Based upon the received initial image, the positioning analysis module and processor of the ECG monitor identifies anatomical landmarks on the patient and generates an outline of the patient's torso. Based upon this analysis, the controller accesses the overlay image module to retrieve an overlay image in step 84. As described previously, the overlay image can include desired locations for each of the ECG electrodes. The overlay image is created and sized based upon the actual patient being viewed by the clinician.

Once the overlay image has been created, the overlay image is shown on the display of the augmented reality device such that the overlay image and the real time image of the patient are simultaneously displayed as indicated in step 86. The simultaneous display of the overlay image and the real time image of the patient on the display of the augmented reality device allow the clinician to view the desired locations of the electrodes while the clinician is viewing the patient.

As the desired locations for the electrodes are shown to the clinician in the augmented image, the clinician can place electrodes on the patient at the visual locations identified. The use of the overlay image thus allows the clinician to be trained and guided into electrode placement while viewing the patient.

Once the electrodes have been positioned in the desired locations, the clinician is instructed to connect the lead wires to each of the electrodes as indicated in step 90. In accordance with the present disclosure, each or the lead wires includes a visual identifier that corresponds to a similar visual identifier on the electrodes. The visual identifiers may be color, reflective images or any other type of indicator that aids in connecting the correct lead wire to the correct electrode.

Once the clinician has finished connecting the lead wires, the method proceeds to step 92 where the camera of the augmented reality device presents an image to the positioning analysis module. The image is analyzed by the positioning analysis module to determine whether all of the lead wires and electrodes are positioned properly. If the lead wires and electrodes are not positioned properly, the method moves to step 94 where the system creates an instruction overlay that is presented to the clinician on the display of the augmented reality device. The instruction overlay may provide instructions to the clinician to switch locations of lead wires. The instruction overlay is created by the positioning analysis module by comparing the visual indicators of the lead wire versus visual indicators on the electrodes. After the instructions have been issued to the clinician in step 94, the clinician is urged to reconnect the lead wires and the electrodes and the method returns to step 92 to again determine whether the lead wires and electrodes are properly positioned. If all of the lead wires and electrodes are properly positioned, the system proceeds to step 96 to begin the ECG procedure.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method of directing positioning of ECG electrodes on a patient by a user, the method comprising:
    providing an augmented reality device having a camera and a display;
    receiving a real time image of the patient from the camera;
    generating an overlay image including visual representations of desired locations for the electrodes;
    displaying the overlay image over the real time image of the patient on the display of the augmented reality device;
    determining an actual location of each of the electrodes placed on the patient by the user based on the real time image;
    determining whether the actual location of each of the electrodes corresponds to the desired location of each electrode;
    providing information to the user on the display to direct the user to adjust the actual location of the electrodes when the actual location does not correspond to the desired location;
    receiving a real time image of the patient after the electrodes have been applied to the patient and lead wires have been connected to the electrodes;
    determining whether the lead wires have been properly connected to the electrodes; and
    providing information to the user on the display of the augmented reality device as to whether the lead wires have been connected properly.

2. The method of claim 1 further comprising the step of recording and storing an image of the actual location of the electrodes when the actual location corresponds to the desired location.

3. The method of claim 1 wherein an image of an actual location of the electrodes is stored for each of a plurality of ECG measurements, wherein the stored images are compared to determine consistency of electrode placement.

4. The method of claim 3 wherein the desired location of each electrode corresponds to the actual location of each electrode during a prior ECG measurement from the patient.

5. The method of claim 1 further comprising the step of recording and storing an image of the actual location of the electrodes and the lead wire connections when the lead wire are connected properly.

6. The method of claim 1 wherein the information provided to the user includes instructions to reposition the lead wires and/or electrodes when the lead wires have not been connected properly.

7. The method of claim 1 wherein the real time image is a video image.

8. The method of claim 7 wherein the overlay image is modified as the real time video image changes.

9. The method of claim 1 wherein the overlay image includes visual representations of anatomical structures and the desired locations of the electrodes.

10. A system for directing positioning of ECG electrodes on a patient by a user, the system comprising:
    an augmented reality device having a camera and a display;
    one or more electrodes; and
    a positioning analysis module executable by a processor to:
        receive a real time image taken with the camera of a patient's chest;
        obtain an overlay image including visual representation of desired locations for the electrodes;
        display the overlay image over the real time image of the patient on the display of the augmented reality device;
        determine an actual location of each of the electrodes on the patient based on the real time image;
        determine whether the actual location of each of the electrodes corresponds to the desired location of each electrode;
        provide information to adjust the actual location of the electrodes when the actual location does not correspond to the desired location;
        receive a real time image of the patient after the electrodes have been applied to the patient and lead wires have been connected to the electrodes;
        determine whether the lead wires have been connected to the electrodes properly; and
        provide information to the user on the display of the augmented reality device as to whether the lead wires have been connected properly.

11. The system of claim 10, further comprising an ECG monitor having a processor configured to execute the positioning analysis module, wherein the augmented reality device is communicatively connected to the ECG monitor.

12. The system of claim 10, wherein the real time image is a video image.

13. The system of claim 10, wherein each of the electrodes have a visual identifier.

14. The system of claim 13, wherein the visual identifier is a predefined color for each electrode.

15. The system of claim 10 wherein the overlay image includes visual representations of anatomical structures and the desired locations of the electrodes.

* * * * *